United States Patent
Liu et al.

(10) Patent No.: US 6,884,422 B1
(45) Date of Patent: Apr. 26, 2005

(54) FREEZE-DRIED HEPATITIS A ATTENUATED LIVE VACCINE AND ITS STABILIZER

(75) Inventors: Jingye Liu, Changchun (CN); Pengfu Wang, Changchun (CN); Guangpu Li, Changchun (CN); Baosheng Xie, Changchun (CN); Zongming Song, Changchun (CN); Shuyan Li, Changchun (CN); Jing Liu, Changchun (CN); Ying Yu, Changchun (CN); Xizhen Guangpu Zhang, Changchun (CN); Ben Liang, Changchun (CN); Lingjiu Liu, Changchun (CN); Wei Wang, Changchun (CN); Ling Zhang, Changchun (CN); Yong Xue, Changchun (CN); Jing Li, Changchun (CN); Yuhong Li, Changchun (CN); Hui Lin, Changchun (CN); Zongju Wan, Changchun (CN)

(73) Assignee: Changchun Institute of Biological Products, Ministry of Public Health (CN)

( * ) Notice: Subject to any disclaimer, the term of this patent is extended or adjusted under 35 U.S.C. 154(b) by 0 days.

(21) Appl. No.: 09/807,783

(22) PCT Filed: Oct. 10, 1999

(86) PCT No.: PCT/CN99/00157

§ 371 (c)(1),
(2), (4) Date: Jun. 1, 2001

(87) PCT Pub. No.: WO00/23104

PCT Pub. Date: Apr. 27, 2000

(30) Foreign Application Priority Data

Oct. 19, 1998 (CN) .................................. 98120633 A

(51) Int. Cl.[7] ..................... A61K 39/29; A61K 39/245; C12N 13/00; C12N 7/00
(52) U.S. Cl. ................... 424/226.1; 424/230.1; 435/173.3; 435/235.1
(58) Field of Search .............. 424/226.1, 230.1, 424/237, 239, 212.1, 204.1, 219.1; 435/173.3, 235.1

(56) References Cited

U.S. PATENT DOCUMENTS

| | | | | | |
|---|---|---|---|---|---|
| 3,557,524 | A | * | 1/1971 | Pratt et al. | 424/89 |
| 4,147,772 | A | * | 4/1979 | McAleer et al. | 424/202.1 |
| 4,338,335 | A | * | 7/1982 | McAleer et al. | 514/777 |
| 5,075,110 | A | * | 12/1991 | Francon et al. | 424/202.1 |
| 5,766,906 | A | * | 6/1998 | Lemon et al. | 435/173.3 |
| 5,888,516 | A | * | 3/1999 | Jansen et al. | 424/204.1 |
| 5,948,411 | A | * | 9/1999 | Koyama et al. | 424/212.1 |
| 6,013,264 | A | * | 1/2000 | Petre et al. | 424/227.1 |
| 6,051,238 | A | * | 4/2000 | Volkin et al. | 424/212.1 |
| 6,113,912 | A | * | 9/2000 | Funkhouser et al. | 424/226.1 |
| 6,180,110 | B1 | * | 1/2001 | Funkhouser et al. | 424/226.1 |
| 6,210,683 | B1 | * | 4/2001 | Burke et al. | 424/230.1 |
| 6,231,860 | B1 | * | 5/2001 | Fanget et al. | 424/184.1 |
| 6,290,967 | B1 | * | 9/2001 | Volkin et al. | 424/204.1 |
| 6,562,350 | B1 | * | 5/2003 | Wang et al. | 424/202.1 |

FOREIGN PATENT DOCUMENTS

| | | |
|---|---|---|
| CN | 1191490 | 8/1998 |
| JP | 1279843 | * 11/1989 |
| WO | 9828000 | 7/1998 |

OTHER PUBLICATIONS

Hollinger et al. Hepatitis A Virus. In B.N. Fields et al. (ed.), Fields Virology, 3rd ed. Philadelphia: Lippencott–Raven Publishers; 1996: 739 and 766–769.*

Chiba–ken et al. (JP 1279843 abstract).*

* cited by examiner

Primary Examiner—Shanon Foley
(74) Attorney, Agent, or Firm—Saliwanchik, Lloyd & Saliwanchik

(57) ABSTRACT

The present invention relates to hepatitis A vaccine, especially to a lyophilized attenuated hepatitis A vaccine which can be stored at ambient temperature for extended periods of time, and to a method for producing the same. The present invention further relates to a stabilizer for lyophilized live vaccine and its use in improving thermostability of lyophilized live vaccine during lyophilization processing and storage period after lyophilization.

10 Claims, No Drawings

FREEZE-DRIED HEPATITIS A ATTENUATED LIVE VACCINE AND ITS STABILIZER

FIELD OF THE INVENTION

The present invention generally relates to attenuated hepatitis A vaccine, and more particularly to a stabilized lyophilized live hepatitis. A vaccine formulation which can be preserved at ambient temperature for extended periods of time, to eliminate the pressures from transportation, storage and usage of the vaccine without loss of infectivity titers of the vaccine. The present invention further relates to a stabilizer for live lyophilized vaccine and its use in producing stabilized lyophilized live vaccine formulations.

BACKGROUND OF THE INVENTION

Hepatitis A is a worldwide distributive acute disease caused by infection with hepatitis A virus (HAV) which is a picornavirus closely related to the poliovirus. Infection is spread by the fecal/oral route and consequently the disease in endemic in areas where hygiene and sanitation standards are lower. Recent reports on epidemical survey show that in developing countries including China, there are as many as 4 million hepatitis A cases per year. There is frequently large-scale outbreak and rapid spread in certain regions with poor social and economic status, especially after various disasters. In these countries or regions, as the high incidence of hepatitis A, some serious public health and social problems have been encountered. On the other hand, in the United States and other developed countries, hepatitis A accounting for approximately 150,000 cases, that is approximately 25% of all clinical hepatitis cases.

Therefore, to successfully immunize against hepatitis A in developing countries as well as in developed countries, it is necessary to vaccinate the entire people, especially entire pediatric populations. So there will be an increasing need for hepatitis A vaccine.

An effective vaccine would be useful for active immunization of populations at high risk. Generally, there are four types of vaccines used for inducing a specific neutralizing antibody against challenge with virus or bacteria: live vaccine, inactivated vaccine, subunit vaccine (component vaccine), and recombinant vaccine. In these vaccines, the live attenuated vaccine could elicit a stronger protective response than others, and could have a significant impact on the eradication of the diseases.

U.S. Pat. Nos. 4,532,215 and 4,636,469 described, respectively a strain of wild-type HAV, designated HM-175, initially isolated from the faces of a patient, and adapted to passage in vitro in African green monkey kidney culture cell and methods for obtaining a vaccine by serial passaging. Also, CN Patent Nos. 89106580.6 and 92114998 disclose the preparation of attenuated HAV designated $H_2$-and L-A-I, respectively.

With regard to live attenuated hepatitis A vaccine, it is worth mentioning the live HAV vaccine based on strain CR*326F (Merck & Co. Inc.), which is under preclinical trials, and the vaccines based on strain $H_2$ and L-A-I, respectively, have been licensed for practical use and industrial-scale production in China. Clinical serological studies demonstrated that these live attenuated hepatitis A vaccines, especially the vaccine prepared from L-A-I strain of HAV (produced by Changchun Institute of Biological Products Ministry of Public Health, Changchun, China) evoked high titers of antibody response, in most volunteers receiving the vaccine, after only one dose and no systemic complains were present immediately after vaccination or during long-term follow-up (see CN Patent No. 92214998).

However, all of the live hepatitis A vaccines used so far are in the form of aqueous suspensions. One of the main disadvantages of live attenuated vaccine is having unsatisfactory thermo-stability, even in the situation of lyophilization at ambient temperature, hence it must be stored and transported in a frozen state and used soon after thawing to insure effective vaccination. Hepatitis A virus, as well as measles virus is unsatisfactory in both storage stability and heat resistance. For example, live attenuated hepatitis A virus survives only for about 7 days at a temperature of 2–8° C., and storage-term duration is only about 3–6 months. Therefore, transportation and storage of these vaccine preparations must be completed at a reduced temperature (e.g., −20° C. or lower), referred to as "cold chain." As a direct result, the increases in production and transportation cost and user's expense are unavoidable, especially in developing countries and tropical and semitropical areas. This cost would be an obstacle to implementation of the worldwide Expanded Program on Immunization (EPI) founded by World Health Organization (WHO).

For the reasons as described above, eradication of hepatitis A will depend on the ability to provide hepatitis. A vaccine formulations having improved thermo-stability. Accordingly, there remains a distinct need in the art for live hepatitis vaccine formulations with enhanced storage stability and heat resistance during and after lyophilization.

SUMMARY OF THE INVENTION

In view of the problems mentioned above, the present inventors have performed intensive experiments during their production practices to overcome these problems and to provide a lyophilized live hepatitis A vaccine with increased thermo-resistance and storage stability. The present inventors have surprisingly found that when a stabilizer solution is added to the vaccine stock suspension prepared by a disclosed method (for example as described in CN Patent No. 92114998), and lyophilized the hepatitis A vaccine formulation comprising, as a virus component, an attenuated live hepatitis A virus and a stabilizer, the storage-term of the hepatitis A virus containing lyophilized vaccine is extended 3 times longer than non-treated stock viral suspension. Therefore, the "cold chain" pressure and user's expense is described greatly thereby increasing the ability for low-cost, widespread use.

It is one object of the present invention to provide a stabilized lyophilized hepatitis A live vaccine formulation comprising a prophylactically effective viral titers of live attenuated hepatitis A virus and a stabilizer which can be preserved at ambient temperature for extended periods of time, so that the "cold chain" pressures from transportation, storage and usage of the vaccine can be reduced or eliminated without loss of infective titers of the vaccine, thereby greatly decreasing the expense and relevant cost to ensure effective widespread vaccination against hepatitis A.

In a preferred embodiment of the present invention, said stock suspension of live attenuated hepatitis A virus is prepared by disclosed method for the wild-type HAV, stain L-A-I.

In a another preferred embodiment of the present invention, said stabilizer for lyophilized live hepatitis A virus is composed of gelatin, trehalose, one or two amino acid selected from the group consisting of glutamic acid, aspartic acid, arginine, lysine or alkali metal salts thereof, ascorbic acid, urea, mannitol or sorbitol or both of them, and inositol.

According to a further preferred embodiment of the present invention, the stabilizer for lyophilized live virus vaccine contains human serum albumin.

In a further preferred embodiment of the stabilizer according to the present invention, the stabilizer for the lyophilized live virus is essentially composed of from 0 to 20 grams per liter of human serum albumin, from 5 to 10 grams per liter of gelatin, from 50 to 100 grams per liter of trehalose, about 7.5 to 15 grams per liter of sodium glutamate, from 0.5 to 5.5 grams per liter of ascorbic acid, from 5 to 28 grams per liter of urea, from 2 to 10 grams per liter of mannitol or sorbitol or a mixture, and from 4 to 10 grams per liter of inositol.

It is another object of the present invention to provide a method of preparing stabilized lyophilized live hepatitis A vaccine formulation as above, comprising:

(a) providing a stock suspension of attenuated live Hepatitis A virus;

(b) adding a stabilizer solution to the stock suspension of step (a) at the ratio 1:1 (v/v) to obtain a live vaccine formulation comprising prophylactically effective viral titers of live attenuated hepatitis A virus and a stabilizer for attenuated live virus, therein said stabilizer comprises gelatin, trehalose, one or two amino acid selected from the group consisting of glutamic acid, aspartic acid, arginine, lysine or alkali metal salts thereof, ascorbic acid, urea, mannitol or sorbitol or both of them, and inositol;

(c) lyophilizing said vaccine formulation obtained from the step (b).

According to a preferred embodiment of this object of the invention, the lyophilization step comprises precooling the vaccine formulation to about −20 to −50° C. over about 3 to 6 hours, and then drying the live vaccine formulation by gradually increasing the temperature from −38 to 35° C. in a lyophilizer.

It is a further object of the present invention to provide a stabilizer for lyophilized live virus, wherein said stabilizer is essentially composed of gelatin, trehalose, one or two amino acid selected from the group consisting of glutamic acid, aspartic acid, arginine, lysine or alkali metal salts thereof, ascorbic acid, urea, mannitol or sorbitol or both of them, and inositol.

According to a preferred embodiment of the present invention, said stabilizer is essentially composed of from 0 to 20 grams per titer of human serum albumin, from 5 to 10 grams per liter of gelatin, from 50 to 100 grams per liter of trehalose, from 7.5 to 15 grams per liter of sodium glutamate, from 0.5 to 5.5 grams per liter of ascorbic acid, from 5 to 28 grams per liter of urea, from 2 to 10 grams per liter of mannitol or sorbital or a mixture of them, and from 4 to 10 gram per liter of inositol.

According to a further preferred embodiment of the present invention, the stabilizer for lyophilized live virus vaccine can contain human serum albumin.

According to preferred embodiment of the present invention, said stabilizer is not only suitable for stabilizing lyophilized hepatitis A live virus, but also used for stabilizing viruses selected from the group consisting of the genus Enterovirus, the genes Paramyxovirus, the genus Arbovirus, and the genus Herpesvirus against heat inactivation during the period of lyophilization and the period of storage and transportation post-lyophilization to ensure thermo-stability of the lyophilized live vaccine thereby to improve vaccination efficacy for susceptible populations.

DETAILED DESCRIPTION OF THE INVENTION

The present invention is related to lyophilized live vaccine formulations having a increased thermo-stability.

Essentially, the vaccine formulations of the present invention are mixtures of virus component and stabilizer components, wherein the virus component comprises hepatitis A virus or at least one member selected from the genuses Enterovirus, Pavamyxovirus, Arbovirus and Herpesvirus, and the stabilizer components comprise gelatin, trehalose, one or two amino acids selected from the group consisting of glutamic acid, aspartic acid, arginine, lysine or alkali metal salts thereof, ascorbic acid, urea, mannitol and/or sorbitol, and inositol. The vaccine stabilizer according to the present invention can contain human serum albumin (HSA) to prevent any undesirable enzymolysis of the virus. Upon mixing the two components in a suitable ratio, the result is a virus formulation which contains from about 0 to 20 grams per liter of HSA, from 5 to 10 grams per liter of gelatin, from 50 to 100 grams per liter of trehalose, from 7.5 to 15 grams per liter of amino acid or alkali metal salts thereof, from 0.5 to 5.5 grams per liter of ascorbic acid, from 5 to 28 grams per liter of urea, about 2 to 10 grams per liter of mannitol or sorbitol or a mixture of them, and from 4 to 10 grams per liter of inositol.

With respect to a attenuated hepatitis A virus, for example, the HAV stock suspension used for the purpose of the present invention could be prepared from the wide-type strain L-A-I by the HAV cell-culture adaption and attenuation method described in CN Patent No. 92114998. Briefly, the method comprises cultivating human diploid fibroblast cells in a suitable nutrient medium, e.g., Eagle's minimal essential medium (MEM), containing 10–15% fetal calf serum (FCS) in a roller bottle at 37° C. for 5–8 days. When confluent cell monolayers are formed, the cultured medium is discarded from the culturing vessel and the cells are washed with the same medium or PBS 3 to 5 times. The cells are inoculated with a seed virus of hepatitis A virus L-A-I derived from human feces and purified by the method of described in Example 1 of CN Patent No. 92114998. The cells are then cultivated in nutrient medium at about 34–36° C. for 3 to 4 weeks After completion of cultivation, the nutrient medium is changed to medium 199 with or without phenol red, and cells are cultivated at 34 to 36° C. for a additional 4 to 6 days in a cell roller. After harvesting, the cells are sonificated 3 times, then the cell debris is removed by centrifugation and the resultant supernatant is collected to obtain the desired stock suspension of the virus.

The present invention further provides a stabilizer advantageously used to stabilize a live vaccine, and to protect attenuated live virus against heat-inactivation at ambient temperature for a extended periods of time, essentially composed of human serum albumin and/or gelatin, trehalose, one or two amino acids selected from the group consisting of glutamic acid, aspartic acid, arginine, lysine or alkali metal salts thereof, ascorbic acid, urea, mannitol and/or sorbitol, and inositol. In a particularly preferred embodiment, the present invention provides a stabilizer containing about 0–20 g/L of HSA, about 5–10 g/L of gelatin, about 50–100 g/L of trehalose, about 7.5–15 g/L of sodium glutamate, about 0.5–5.5 g/L of ascorbic acid, about 5–28 g/L of urea, about 2–10 g/L of mannitol and/or sorbitol, and 4–10 g/L of insoitol.

Hepatitis A virus is a small picornavirus with no outer envelope or other lipids. Like the majority of live enteroviruses, hepatitis A virus presented in form of aqueous suspension will rapidly lose the ability of replication, propagation, and/or infectious potency. In the absence of a suitable stabilizer, effective protection against hepatitis A infection is extremely susceptable to heat inactivation of the virus. Thus eradication of hepatitis A and other epidemic caused by infection with virus will depend on the ability to assure cold storage and transportation of virus vaccine. However, according to the present invention, this problem has been circumvented by using vaccine formulations with improved stability characteristics.

Vaccine stabilizers are well known in the art as chemical compounds added to vaccine formulations to enhance vaccine stability during periods of low temperature storage, lyophilization processing, or storage post-lyophilization. As described above, the stabilizer aqueous solutions used for formulating and stabilizing the live vaccine of the present invention are preferably composed of a high molecular weigh structural additive, a disaccharide, a sugar, alcohol and water. The aqueous solution also includes one or two amino acids and a buffering component. The combination of these components act to preserve the survival and activity of the virus upon freezing and lyophilization and a long storage period subsequent to lyophilization.

It is well known that high molecular weight structural additives aid in preventing viral aggregation during freezing, and provide structural and nutritional support in the lyophilized or dried state. Within the context of the present invention, the preferred high molecular weight structural additives are human serum albumin and/or gelatin. The amino acids, sugars, and alcohols function to further preserve viral infectivity upon cooling and thawing of the aqueous suspension. In addition, these components function to preserve viral infectivity during sublimation of cooled aqueous virus suspensions during lyophilization and in lyophilized state, and contribute some buffering ability. The preferred amino acids are arginine and glutamate, and the preferred sugar alcohols are mannitol, sorbitol and inositol. Trehalose is the preferred disaccharide used in the stabilizer aqueous solution and could be extremely beneficial for stabilizing the protein structure of the virus to increase heat-resistance and for restoring the potency of the virus after dehydration. Urea and ascorbic acid play an important part in stabilizing the hydration state or in maintaining osmotic balance during dehydration period. The buffering component acts to buffer the formulation by maintaining a relatively constant pH which is preferably about 7.0. The preferred buffer is balanced salt solution or PBS used for dissolving the chemical compounds disclosed above.

The components are added in increasing amounts to generate vaccine stabilizer to combine with viral stock suspensions to generate vaccine formulations for lyophilization that have an increased increase in thermo-stability. The preferred component ranges disclosed in this specification allow for generation of vaccine formulations which, among other characteristics, exhibit improved thermo-stability over vaccine formulations known in the art.

The stabilizer of live attenuated vaccine can be formulated by conventional methods, for example, by mixing each of the components in a suitable vessel, except for preheating the mixture solution of trehalose, gelatin, urea, mannitol and/or sorbitol at about 37° C. for 24 to 28 hours before adding HSA thereto. After 0.5 to 2 hours, mixing the resultant stabilizer is mixed with viral stock at about 1:1 (v/v) ratio.

It is noteworthy that the ranges of virus stabilizer and final vaccine formulation are presented on a gram per liter basis of the final vaccine formulation. One of ordinary skill in the art will be well aware that changing volume ratio of stabilizer to vaccine may be applied to practice the claimed invention, which in turn will require changes to the concentration of stabilizer components. Therefore, the invention is not only limited to the specified 1:1 stabilizer/virus combination to generate the final vaccine formulation for lyophilization.

After the vaccine is formulated with stabilizer and viral stock, the resultant aqueous suspension should be dried by lyophilization. Briefly, the lyophilization cycles involves the steps of precooling the aqueous suspension below the gas transition temperature or below the eutectic point temperature (below −30° C.) of the aqueous suspension for 3 to 6 hours, and then removing water from the cooled suspension by sublimation to form a lyophilized virus. Within one preferred embodiment, aliquots of the formulated attenuated live virus are placed into a refrigerated chamber attached to a freeze dryer. A multistep freeze drying procedure is used in lyophilizing the formulated live vaccine. The temperature is then gradually increased from about −38° C. to about 35° C. over a period of 10 to 20 hours.

In order to demonstrate improvement in thermal stability and storage stability of live vaccine, the present invention is exemplified by viral potencies, for example for detecting viral titers pre- and post-lyophilization of hepatitis A vaccine, and to observe the effectiveness of a stabilizer on the storage stability of live vaccine. The results show that the stabilizer included in the vaccine formulations of the present invention at a concentration sufficient to stabilize the live virus vaccine against heat inactivation remarkably improved thermal stability of the virus which had been lyophilized and incubated at 37° C. for one week as measured by the log $CCID_{50}$, as compared with lyophilized control vaccine formulation which is absent of stabilizer.

Further, the present inventors in a comparison experiment found that a similar result can be observed when a stabilizer solution, which does not contain the human serum albumin (HSA) component, is used for the live virus vaccine if the lyophilization cycle parameters could be suitably adjusted.

The following examples are provided to illustrate the present invention. It is to be understood, however, that the examples are not to limit the scope of the present invention.

EXAMPLE 1

Preparation of stabilizer (I) in accordance with the present invention for lyophilized live virus:

Following components are utilized for formulating the stabilizer solution (I):

| Component | Amount (g/L) |
|---|---|
| Human Serum Albumin | 10.0 |
| Gelatin | 5.5 |
| Trehalose | 65.0 |
| Sodium Glutamate | 10.0 |
| Urea | 20.0 |
| Ascorbic Acid | 5.5 |
| Sorbitol | 6.6 |
| Inositol | 7.5 |

300 ml of distilled water is added to 5.5 g of purified gelatin, and the resultant mixture is heated for 40 minutes in an autoclave (116° C.) to obtain a solution. The resulting solution is cooled to a temperature of about 30–35° C., and 10.0 g of HSA sterilized by ultrafiltration, is added. In according with the formulation as above, corresponding amount of trehalose, sodium glutamate, urea, ascorbic acid, sorbitol and inositol are added in this order, to 500 ml of distilled water and thoroughly mixed. The resultant solution is heated for 24 hours at 37° C. After cooling the solution to ambient temperature (about 22–26° C.), the solution is placed into gelatin-HAS solution and mixed thoroughly. Subsequently, distilled water is added to bring the total volume to 1000 ml. The pH of the resulting mixture solution is adjusted to about 7.0 by 0.1 N HCL, and is subjected to filtration sterilization once again, to obtain a stabilizer solution (I) which could be used for stabilizing live virus, to be lyophilized and stored.

EXAMPLE 2

Preparation of stabilizer (II) for lyophilized live vaccine:

The following components are utilized for formulating the stabilizer solution (II) in accordance with the present invention, by a procedure similar to that described in Example 1.

| Component | Amount (g/L) |
|---|---|
| Gelatin | 8.5 |
| Trehalose | 75.0 |
| Urea | 15.5 |
| L-arginine | 10.1 |
| Ascorbic Acid | 3.0 |
| Sorbitol | 5.0 |
| Mannitol | 5.0 |
| Inositol | 4.0 |

HSA is eliminated as the component because it is very expensive and may cause virus contamination derived from collected blood sources. Furthermore, the sodium glutamate is replaced by arginine or alkali metal salt thereof, and a small amount of inositol is added thereto.

EXAMPLE 3

Preparation of stabilized lyophilized hepatitis A live vaccine:

Essentially, the stock suspension of hepatitis A live vaccine can be prepared by the method described in detail in CN Patent No. 92114998. Briefly, propagating human fetal lung diploid fibroblast cells infected with HAV strain L-A-I derived from human faces, which strain had been established by Dr. Wang Penfu and his colleague in Changchun Institute of Biological Products, Ministry of Public Health, Changchun, China, in appropriate virus infectious dose in minimum essential medium (MEM) containing 10% fetal calf serum (FCS) at 37° C. for 3 to 4 weeks by serial passaging. When the amount of positive infected cells is more than 90% as detected by indirect immunofluorescence technique. The nutrient medium is discarded from culturing vessel, and the residual FCS is washed away by phosphate-buffered saline (BPS). The cultured medium replaced by medium 199 without phenol red therein, and the infected cells are cultivated for a additional 4 to 6 days. After completion of the culturing and collecting the infected cells by low-speed centrifugation, the infected cells are disrupted by means of 3 cycles of freeze-thawing and sonification. Cellular debris is removed by centrifugation and the supernatant is collected as a stock of the vaccine. The stock material (suspernatant product) will give a positive result for antigen by indirect immunoflurescence assay.

After the hepatitis A vaccine is formulated by mixing the stabilizer solution (I) prepared in Example 1 and viral stock suspension prepared as stated above at about 1:1 (v/v) ratio, the resultant vaccine formulation is divided into a small volumes (0.5 ml) into 2 ml glass vial. And then the aliquots of the formulated viral vaccine are placed into a freeze dryer (model FS150-SS20C, Hull Co., USA) for multistep lyophilization cycle at −40° C. for 4 hours, and then the shelf temperature is gradually increased to about −30° C. and maintained primary drying. The shelf temperature is then gradually increased to 32° C. and maintained there for 15 hours to obtain desired lyophilized stabilized hepatitis A vaccine formulation with a very low moisture content.

EXAMPLE 4

Preparation of stabilized lyophilized measles live vaccine:

The stock suspension of attenuated live measles vaccine is prepared in accordance with the Requirement of Measles Vaccine, Live in Chinese Requirements for Biological Products. The stock material is mixed with the stabilizer solution (II) prepared in Examples 2 at 1:1 (v/v) ratio to obtain measles live vaccine formulation. The vaccine formulation is precooled at −40° C. for 5 hours, and then the formulation is subjected a drying treatment at about −35° C. to 34°0 C. for 14 hours to result in the lyophilized stabilized measles live vaccine.

EXAMPLE 5

Storage stability testing of lyophilized hepatitis A live vaccine:

The samples of lyophilized hepatitis A live vaccine from different lots of viral formulation prepared in Example 3 which are stored at 2–8° C. for 3 to 12 months, are ten-fold serially diluted, then the sample of $10^{-2}$ to $10^{-7}$ dilution is used for detecting the viral titers every three months. The vaccine formulation from the same lot and lyophilized by the same lyophilization cycle parameters without stabilizer is used as a control sample. After adding distilled water for injection to the lyophilized vaccine for reconstitution, the resultant aqueous suspension containing the live virus and stabilizer is subjected to testing for storage-stability by determinating viral titers ($CCID_{50}$) using conventional enzyme linked immunosorbent assay (ELISA) and indirect-immunofluorescence assay (IF). The results of the testing reveal that the 5 lots of samples which were lyophilized in the presence of stabilizer solution exhibited higher infectious titers in the range from about 6.33 to about 6.50 log $CCID_{50}$, whereas the 5 lots of control samples lyophilized in the absence of stabilizer solution exhibited remarkably decreased infectious titers in the range from about 1.33 to 2.33 log $CCID_{50}$.

In another experiment, the lyophilized virus samples from the same lot of vaccine formulations were stored at 2–8° C., 25° C. and 37° C., respectively, and each of the samples were sampled every day and subjected to testing for storage stability in terms of lowest valid storage periods by detecting the $CCID_{50}$ values. Live vaccine in the form of aqueous suspension are compared to lyophilized vaccine formulation.

The results are summarized in Table 1 to Table 2 below, respectively.

TABLE 1

Storage stability test of lyophilized live hepatitis A vaccine formulation with stabilizer:

| Lot number | Months of storing at 2–8° C. | | | | |
|---|---|---|---|---|---|
| of sample | 0 | 3 | 6 | 9 | 12 |
| 1 | 6.50* | 6.67 | 6.67 | 6.50 | 6.50 |
| 2 | 6.67 | 6.50 | 6.67 | 6.50 | 6.67 |
| 3 | 6.50 | 6.50 | 6.33 | 6.50 | 6.50 |
| 4 | 6.50 | 6.67 | 6.67 | 6.50 | 6.33 |
| 5 | 6.33 | 6.50 | 6.50 | 6.50 | 6.33 |
| control sample | 2.33 | 1.75 | 1.50 | 1.50 | 1.33 |

*Infective titers of the virus (log $CCID_{50}$/ml)

TABLE 2

Comparison of stability of hepatitis A live vaccine:

| Temperature of storage | Lowest valid storage period (days) | |
|---|---|---|
| | Aqueous suspension | Lyophilized formulation |
| 2–8° C. | 180 | 360 |
| 25° C. | 7 | 90 |
| 37° C. | 1 | 7 |

It can be seen from the results shown in Table 1 and Table 2 as above, that the stabilizer for lyophilized live vaccine of the present invention greatly increased thermo-stability measured as the log $CCID_{50}$, due to the stabilized structure of viral protein and nucleic acid, and effectively maintains viral potency of the vaccine under the conditions of increased temperature and osmotic strength.

EXAMPLE 6

The Immunogenicity and Safety Testing of the Lyophilized Hepatitis A Live Vaccine:

The lyophilized hepatitis A live vaccine formulation prepared in accordance with the method in Example 1 which has been stored at about 25° C. for 30 days is intravenously inoculated into healthy rhesus monkeys (each group comprising 5 animals). Every two weeks the monkeys were bled for 8 weeks and checked for abnormally elevated serum enzymes (GPT) levels and the titers of anti-HAV antibody. Abnormal elevations of enzymes (more than 25U/ml) would indicate the presence of hepatitis A disease in the animals and the presence of antibody would shown protection (Table 3). In this experiment, a fresh vaccine preparation in initial state from the same lot but which is unlyophilized and without stabilizers therein is used as a control sample. All of the animals received a $10^{(6.5)}$ $CCID_{50}$ viral infectious dose (1.0 ml of the stock). The results are summarized in Table 3 below.

TABLE 3

Serum GPT abnormal elevation and antibody response of animals before and after inoculation with the lyophilized hepatitis A vaccine.

| | Abnormal elevation of SGPT* | | | | anti-HAV IgG Ab** | | | | anti-HAV IgM Ab** | | | |
|---|---|---|---|---|---|---|---|---|---|---|---|---|
| Lots | 0 | 2 | 4 | 8(w) | 0 | 2 | 4 | 8(w) | 0 | 2 | 4 | 8(w) |
| 1 | 0/5 | 0/5 | 0/5 | 0/5 | 0 | 60 | 100 | 100 | 0 | 60 | 40 | 0 |
| 2 | 0/5 | 0/5 | 0/5 | 0/5 | 0 | 40 | 100 | 100 | 0 | 80 | 40 | 0 |
| 3 | 0/5 | 0/5 | 0/5 | 0/5 | 0 | 60 | 80 | 100 | 0 | 60 | 40 | 20 |
| 4 | 0/5 | 0/5 | 0/5 | 0/5 | 0 | 60 | 60 | 100 | 0 | 80 | 20 | 0 |

*Serum GPT value $\geq$ 25 U/ml is considered to be abnormal elevation of the enzyme.
**The data given in the table represent percentage seroconvertion rates from 4 animals.

It is can be seen from the results showed in Table 3, that all rhesus monkeys developed anti-HAV protective antibody and more than 80% of seroconverted animals also developed IgM anti-HAV at about two weeks after inoculation. On the other hand, none of the rhesus monkeys had elevated liver enzymes atributable to the vaccination. All values for these higher primates were within normal limits. This indicates no biochemical evidence of hepatitis. These results exhibited comparable immunogenicity and safety with control samples, and show that the lyophilized live vaccine formulation of the present invention which has been stored for 30 days at ambient temperature still maintains a similar immunogenicity and safety to its initial state.

EXAMPLE 7

Storage-stability of lyophilized measles live vaccine:

Storage-stability testing of measles live vaccines pro- and post-lyophilization stored at 2–8° C. and 37° C., respectively, were performed in substantially the same manner as described in Example 5.

The results show that, in the presence of stabilizer of the present invention, 5 lots of measles vaccine exhibited a slightly decreased themostability subsequent to lyophilization, that is less than 0.5 log loss in comparison to the control vaccine in initial state. Further, the lyophilized measles vaccine sample stored at 2–8° C. for 15 months and at 37° C. for 4 weeks had a $CCID_{50}$ reduced by 0.5 and 1.0, respectively.

What is claimed is:

1. A stabilized lyophilized hepatitis A live vaccine formulation comprising prophylactically effective titers of live attenuated hepatitis A virus and a stabilizer, wherein said live attenuated hepatitis A virus is prepared from the wild-type HAV, strain L-A-I, and wherein said stabilizer is present in the vaccine formulation at a concentration sufficient to stabilize the hepatitis A virus against heat inactivation.

2. A stabilized lyophilized hepatitis A live vaccine formulation according to claim 1, wherein said stabilizer for lyophilized live hepatitis A virus comprises human serum albumin or gelatin or both of them; trehalose; at least one amino acid selected from the group consisting of glutamic acid, aspartic acid, arginine, lysine, and alkali metal salts of any of the foregoing; ascorbic acid; area; mannitol or sorbitol or both of them; and inositol.

3. A stabilized lyophilized hepatitis A live vaccine formulation according to claim 1, wherein said stabilizer for the lyophilized live virus comprises from 0 to 20 grams per liter of human serum albumin, from 5 to 10 grams per liter of gelatin, from 50 to 100 grams per liter of trehalose, from 7.5 to 15 grams per liter of sodium glutamate, from 0.5 to 5.5 grams per liter of ascorbic acid, from 5 to 28 grams per liter of urea, from 2 to 10 grams per liter of mannitol or sorbitol, and from 4 to 10 grams per liter of inositol.

4. A method of preparing stabilized lyophilized live hepatitis A vaccine formulation according to claim 1, comprising:

(a) providing a stock suspension of attenuated live Hepatitis A virus, wherein said live attenuated hepatitis A virus is prepared from the wild-type HAV, strain L-A-I;

(b) adding a stabilizer solution to stock suspension of attenuated live hepatitis A virus obtained from step (a) at the ratio 1:1 (v/v) to obtain a live vaccine formulation comprising prophylactically effective titers of live attenuated hepatitis A virus and a stabilizer for attenuated live virus, wherein said stabilizer comprises gelatine; trehalose; at least one amino acid selected from the group consisting of glutamic acid, aspartic acid, arginine, lysine, and alkali metal salts of any of the foregoing; ascorbic acid; urea; mannitol or sorbitol or both of them; and inositol; and (c) lyophilizing said vaccine formulation obtained from the step (b).

5. The method according to claim 4, wherein said lyophilizing step comprises pre-cooling the vaccine formulation to about −20° C. to −50° C. for about 3 to 6 hours, then drying the live vaccine formulation by gradually increasing the temperature to at least 32° C. in a lyophilizer.

6. The method according to claim 4, wherein said stabilizer comprises from 0 to 20 grams per liter of human serum albumin, from 5 to 10 grams per liter of gelatin, from 50 to 100 grams per liter of trehalose, from 7.5 to 15 grams per liter of sodium glutamate, from 0.5 to 5.5 grams per liter of ascorbic acid, from 5 to 28 grams per liter of urea, from 2 to 10 grams per liter of mannitol or sorbitol, and from 4 to 10 grams per liter of inositol.

7. The method according to claim 4, wherein said lyophilizing step comprises pre-cooling the vaccine formulation to about −20° C. to −50° C. for about 3 to 6 hours, then drying the live vaccine formulation by gradually increasing the temperature to at least 32° C. in a lyophilizer; and wherein said stabilizer comprises from 0 to 20 grams per liter of human serum albumin, from 5 to 10 grams per liter of gelatin, from 50 to 100 grams per liter of trehalose, from 7.5 to 15 grams per liter of sodium glutamate, from 0.5 to 5.5 grams per liter of ascorbic acid, from 5 to 28 grams per liter of urea, from 2 to 10 grams per liter of mannitol or sorbitol, and from 4 to 10 grams per liter of inositol.

8. A stabilizer for lyophilized live virus, wherein said stabilizer comprises gelatin; trehalose; at least one amino acid selected from the group consisting of glutamic acid, aspartic acid, arginine, lysine, and alkali metal salts of any of the foregoing, ascorbic acid; urea; mannitol or sorbitol or both of them; and inositol.

9. A stabilizer according to claim 8, wherein said stabilizer comprises from 0 to 20 grams per liter of human serum albumin, from 5 to 10 grams per liter of gelatin, from 50 to 100 grams per liter of trehalose, from 7.5 to 15 grams per liter of sodium glutamate, from 0.5 to 5.5 grams per liter of ascorbic acid, from 5 to 28 grams per liter of urea, from 2 to 10 grams per liter of mannitol or sorbitol, and from 4 to 10 grams per liter of inositol.

10. A stabilizer according to claim 8, wherein said lyophilized live virus is selected from the genus Enterovirus.

* * * * *